June 23, 1959 F. HARTMAN Plant Pat. 1,848
STRAWBERRY PLANT
Filed Aug. 18, 1958
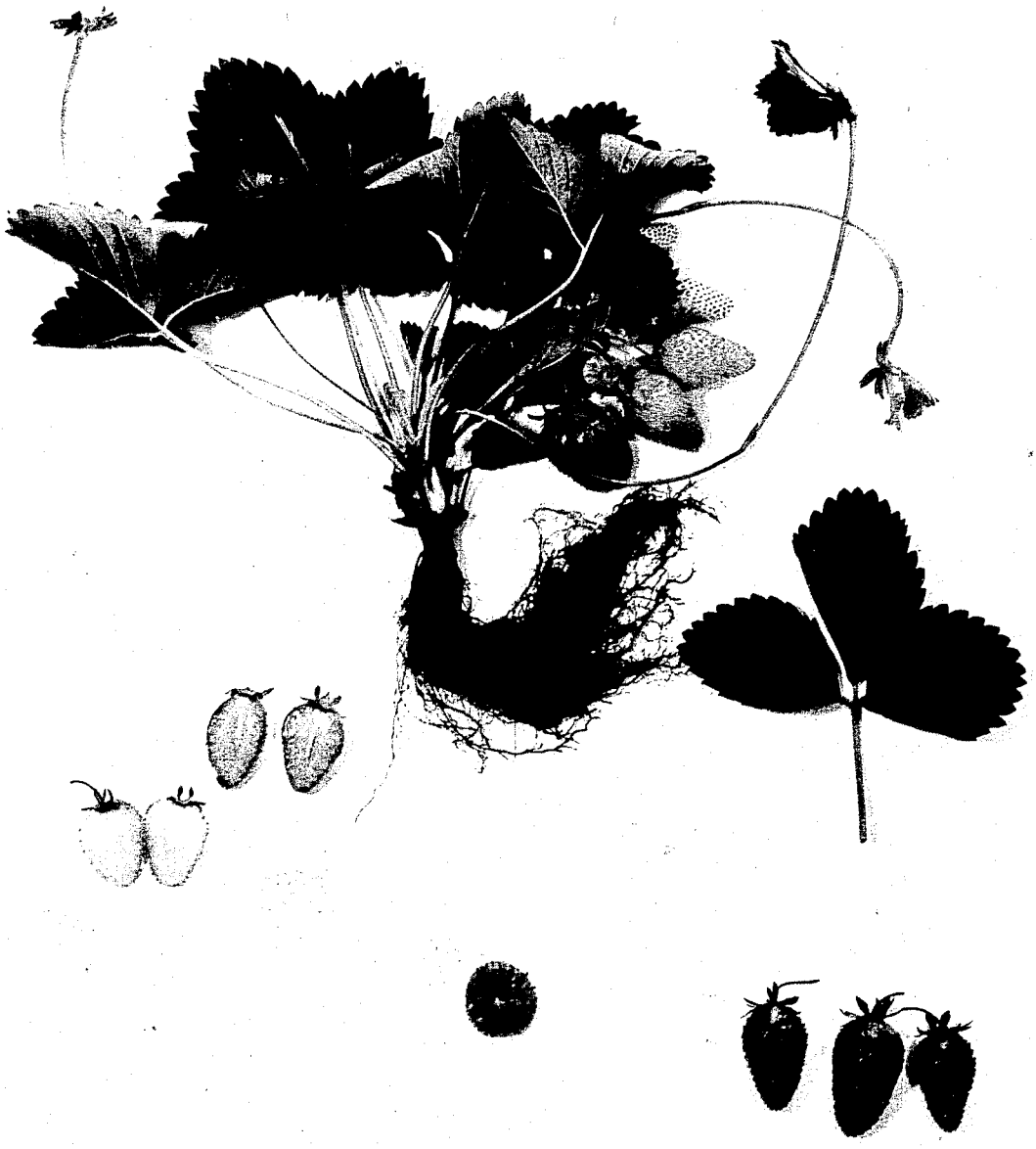
INVENTOR
FLOYD HARTMAN
BY Ludlow E. Mills United States Patent Office Plant Pat. 1,848
Patented June 23, 1959

1,848

STRAWBERRY PLANT

Floyd Hartman, Stanton, Mich., assignor to John H. Rhoades and Evelyn E. Rhoades, both of Lansing, Mich.

Application August 18, 1958, Serial No. 755,813

1 Claim. (Cl. 47—62)

This invention relates to a new and distinct variety of strawberry plant.

The original plant was discovered by me on June 17, 1953, growing on my property in Moncalm County, Michigan, between beds of Robinson and Premier varieties of strawberry plants, neither of which is believed to be patented. The original plant was a rooted runner from a parent plant in the Premier bed but it is not known whether or not the parent plant was a typical plant of the Premier variety. Consequently, although it is thought that the original plant was a sport or mutant of the Premier variety, it cannot be said with certainty that it was not the result of a cross between the Premier and Robinson varieties.

Because of the unique and distinctive characteristics exhibited by the discovered plant, I reproduced it asexually on my property in Montcalm County, Michigan, by transplanting rooted runners from it. Asexual reproduction was continued in this manner through several successive generations without any indication of deterioration of the variety or of change in its distinctive and unique characteristics. It has thus been shown that the distinctive and unique characteristics are established and come true through succeeding generations. As will be seen from the following description, the new variety embodies desirable characteristics not heretofore known.

The accompanying drawing shows a plant, a leaf, sectional views of the fruit through the calyx seat at different stages of ripeness and a view of the calyx end of a fruit, all views being of typical specimens of the new variety and in color as nearly true as is reasonably possible to make color illustrations of this sort.

The plant of the new variety is of especially vigorous growth with a well developed root system. The runners are exceptionally numerous and long and many develop even before ripening of the fruit. The trifoliate leaves are borne on strongly upright stems affording a minimum of shading of the fruit. The leaflets are darker green and somewhat larger and relatively broader than those of the Premier variety. The leaflets are lobed somewhat more nearly to the base than those of the Premier variety, the individual lobes being more rounded than those of the Premier variety with a small and pointed tip resembling those of the Robinson variety in this respect.

The cymose white flowers are borne on sturdy pale reddish stems which exhibit a strong tendency to support the flowers and fruit mostly off the soil. The new variety is somewhat less free blooming than either the Robinson or Premier varieties but produces a larger proportion of large, first class marketable fruit than either of these varieties so that its yield is at least equal to that of the Robinson. The season of fruiting is about the same as that of the Premier variety. The blossoms exhibit at least as much tolerance to frost as those of the Premier variety.

The fruit of the new variety is sweet, with a rich flavor and aroma, but slightly milder than the Premier variety. When ripe, the skin and flesh of the fruit are a moderate to slightly deeper red (Plate 2.5–R 4/10 of the Nickerson Colorfan: Maximum Croma 40 Lines; distributed 1957 by the American Horticultural Council), the color developing evenly entirely through the fruit even before full ripening. The skin of the fruit is shiny and the shiny yellow seed-like achenes are indented so that they protrude only very slightly, or not at all, above the skin.

The fruit is characteristically elongated and conical in shape, being narrowly rounded at the tip end and broadly rounded at the stem end. The early fruit is large, often 1¾ to 2 inches long, with the later picked fruit being medium to large in size. The fruit is very regular in shape, being essentially circular in horizontal cross section between the ends, without grooves or irregularities except for a very few early fruits which may be double. The calyx seat at the broadly rounded end of the fruit is characteristically non-recessed and is often slightly protuberant. The sepals flare from the calyx seat in characteristic fashion, usually entirely away from the surface of the fruit, thus encouraging even color development clear up to the calyx seat. Because of the characteristic arrangement of the calyx seat and sepals, the fruit of the new variety is exceedingly well adapted to mechanical stemming.

The fruit is entirely coreless and free from fibers. In the sectioned fruit a core-like outline can often be seen, especially in the green fruit, but there is no tendency for this to develop into an actual core or for the coloring of the ripe fruit to be more than slightly irregular through its central parts. Even the early fruits are almost invariably solid throughout and free of hollow spaces such as often occur in the early fruits of the Premier variety.

The fruit is firm and stands up well under shipping. Because of its coreless and fiber-free characteristics, it is excellent for use in processing procedures which involve pulping of the fruit, as in the preparation of jams and the like.

I claim:

A new and distinct variety of strawberry plant substantially as herein shown and described, characterized by a large, essentially coreless, non-fibrous fruit, rich in flavor and aroma and with indented achenes; by the substantially uniform development of a moderate to slightly deeper red color entirely through the skin and fruit during ripening; by the highly regular contour of the fruit which is essentially that of an elongated cone, being practically circular in transverse cross section between its stem and tip ends, narrowly rounded at the tip end and broadly rounded at the stem end; and by the non-recessed character of the calyx seat and the flaring of the sepals away from the surface of the fruit around the calyx seat in the ripened fruit.

No references cited.